United States Patent [19]

Savage et al.

[11] Patent Number: 5,271,932
[45] Date of Patent: Dec. 21, 1993

[54] *XANTHOMONAS CAMPESTRIS* ISOLATES AND METHODS OF USE

[75] Inventors: Steven D. Savage, San Marcos; Robert A. Haygood, San Diego, both of Calif.

[73] Assignee: Mycogen Corporation, San Diego, Calif.

[21] Appl. No.: 983,183

[22] Filed: Nov. 30, 1992

Related U.S. Application Data

[62] Division of Ser. No. 753,270, Aug. 30, 1991, Pat. No. 5,192,541.

[51] Int. Cl.$^5$ .................... A01N 63/00; A61K 37/00; C12N 1/00
[52] U.S. Cl. ........................ 424/93 R; 424/93 D; 435/243; 504/117
[58] Field of Search .................. 424/93 R, 93 D; 435/243; 504/117

[56] References Cited

FOREIGN PATENT DOCUMENTS 0374499 11/1989 European Pat. Off.
8801172  2/1988 PCT Int'l Appl.

OTHER PUBLICATIONS

Roberts, David L., Karen K. Baker, and Joseph M. Vargas, Jr. (1983) "Scanning Electron Microscopy as a Rapid Diagnostic Aid in the Study of the Etiology and Distribution of Bacterial Wilt of Toronto Creeping Bentgrass" Scanning Electron Microsopy 4:1719–1722.
Egli, T., and D. Schmidt (1982) "Pathogenic Variation among the Causal Agents of Bacterial Wilt of Forage Grasses" Phytopath. Z. 104:138–150.
Roberts, D. L., J. M. Vargas, Jr., D. W. Fulbright, and K. K. Baker (1984) "Characterization of the Bacterium Causing Bacterial Wilt of Toronto Creeping Bentgrass" Phytopathology 73:810. *abstract*.
McWhorter, C. G. (1984) "Future Needs in Weed Science" Weed Science 32:850–855.
Roberts, D. L., J. M. Vargas, Jr., R. Detweiler, K. K. Baker, G. R. Hooper (1981) "Association of a Bacterium with a Disease of Tornonto Creeping Bentgrass" New Diseases and Epidemics 65(12):1014–1016.
Roberts, D. L., J. M. Vargas, Jr., R. Detweiler, K. K. Baker (1982) "Symptom Suppression with Oxytetracycline of a Toronto Creeping Bentgrass Disease of Presumed Bacterial Etiology" Plant Disease 66(9):804–806.
Roberts, D. L., and J. M. Vargas, Jr. (1984) "Antigenic Relatedness of the North American Toronto Bentgrass Bacterium to *Xanthomonas Campestris* PV. *Graminis* From Europe" Phytopathology 74:813. *abstract*.
Roberts, D. L., J. M. Bargas, Jr., and R. Detweiler (1984) "Occurrence of Bacterial Wilt on *Poa Annua* and Other Turfgrasses" Phytopathology 75:1289. *abstract*.
Ming, Di, Huazhi Ye, N. W. Schaad, and D. A. Roth (1991) "Selective Recovery of Xanthomonas Spp. From Rice Seed" Phytopathology 81(11):1358–1363.
Masutani, Tetsuya (1987) "Novel Microorganism Showing Herbicidal Activity" Patent Abstracts of Japan 12(172):497.

*Primary Examiner*—Douglas W. Robinson
*Assistant Examiner*—L. Blaine Lankford
*Attorney, Agent, or Firm*—Saliwanchik & Saliwanchik

[57] ABSTRACT

The subject invention pertains to novel microorganisms useful for the control of unwanted grasses and other weeds. The microorganisms of the subject invention are discovered through a unique process which involves isolating plant pathogens from asymptomatic plants.

6 Claims, 1 Drawing Sheet

XANTHOMONAS CAMPESTRIS ISOLATES AND METHODS OF USE

This is a division of application Ser. No. 07/753,270, filed Aug. 30, 1991 now U.S. Pat. No. 5,192,541.

BACKGROUND OF THE INVENTION

Beneficial uses of microorganisms are well known in the art and have been documented at great length. Many patents have issued which claim new microbial processes pertaining to the production of antibiotics, enzymes, ethanol, and a multitude of other useful products. Microorganisms are also used to clean up toxic wastes and oil spills, kill pests, recover minerals, and provide nutrients to plants. It has been known for many years that some organisms produce compounds which are toxic to other organisms. The production of the antimicrobial compound penicillin by penicillium mold is one such example.

Microorganisms are particularly attractive candidates for use in making and delivering organic compounds because they can be extremely efficient and safe. The modern tools of genetic engineering have greatly enhanced the ability to exploit the efficiency and relative safety of microbes. Even in the absence of genetic manipulation, however, microbes can perform highly specific tasks which make them indispensable in certain applications. Thus, there is a constant ongoing search in many areas of research for previously unknown microbes with specific advantageous properties. The subject invention concerns the discovery of such microbes.

Weeds are a tremendous problem for farmers throughout the world. Weeds cause a 10-12% loss of value for agricultural products in the United States, the most recent estimate being $20 billion annually (McWhorter, C. G. [1984] Weed Sci. 32:850-855).

Undesirable grasses are a significant problem to homeowners, golf courses, and agriculture workers. Chemical control of these grasses may pollute the environment and often does not provide the necessary selectivity to kill pest grasses without harming desirable vegetation.

There exist multiple societal pressures for the replacement of chemical pesticides with alternate control methods. One area of active research along these lines involves the use of plant pathogens which can attack weeds. Although the existence of these pathogens is well known, and some of these pathogens have been patented, there are very few commercial products utilizing bioherbicides and these enjoy only limited use. For the most part, the organisms employed have been fungal pathogens with a much more limited effort having been directed towards bacterial pathogens. The process for finding such "bioherbicide" pathogens has a low success rate for yielding commercially applicable discoveries.

Microorganisms can be associated with plants in many ways. For example, some are saprophytic and some are pathogenic, but even those which are pathogens may exist only rarely in a phase of their life cycle or epidemiological event in which signs or symptoms of disease are evident. Many organisms which can be pathogenic under certain circumstances exist as epiphytes or endophytes on or in plants which are "healthy". These associations have been documented in the literature.

Some bacteria are known to infect certain grasses causing the grasses to be suppressed or killed. These infections have been known in various geographic locations as important problems for the maintenance of desirable grasses. A bacterial infection of Toronto creeping bentgrass which is used on golf putting greens is described by Roberts, D. L., et al. in Plant Disease 65, 1014-1015 (1981); Roberts, D. L., et al., Plant Disease 66, 804-806 (1982); Roberts, D. L., et al., Scanning Electronic Microscopy IV, 1719-1722 (1983). The bacterium was identified as a *Xanthomonas campestris* by Roberts, D. L. in Phytopathology 73, 810 and 74, 813 (1984). The solution to the problem was treatment of the infection with oxytetracycline, an antibiotic. A disease of *Poa annua* L. was also described by Roberts, D. L. in Phytopathology 75 1289 (1985). The organism causing this disease has been deposited as NRRL B-18018 and is designated herein as MB218. In their 1982 paper, Egli and Schmidt described three new pathovars of *Xanthomonas campestris* which caused wilt diseases of forage grasses. Previously all such wilt organisms were classified as *X. campestris* p.v. *graminis*, but by studying a large collection of isolates, these workers found some isolates with much narrower host ranges than the typical, *graminis* pathogens. One of these, p.v. *poae*, (ATCC 33804; MB238) was shown to cause wilting in only a few species of the genus Poa, most notably *Poa trivialis* or rough bluegrass.

BRIEF SUMMARY OF THE INVENTION

The novel microorganisms of the subject invention have been discovered using a novel method for isolating microbes which are useful for the control of weeds. According to this method, microbes are isolated from asymptomatic plants. The microbes can then be grown and applied in greater concentrations to either the original host or other target weeds. Useful weed pathogens discovered using the method of the subject invention are described herein.

The present invention further relates to a method for controlling weed grasses by infecting them with a *Xanthomonas campestris* pathovar which does not kill non-weed grasses. In one preferred embodiment of the invention, the bacterial pathogens benefit from direct access to the xylem of the target weed. Access to the xylem generally requires a wound to the target plant. In one specific embodiment of the subject invention, weed grasses are controlled rapidly and effectively with a treatment of a *Xanthomonas campestris* pathovar. The control is facilitated by cutting the weed grass either before or after application of the bacteria.

The microbes of the subject invention can also be transformed with genes coding for various toxins and then re-applied to vegetation. The toxins may be, for example, from *Bacillus thuringiensis*. Because of their ability to colonize plants, the novel microbes are useful for delivery of the desired toxin.

DETAILED DESCRIPTION

Figure 1:
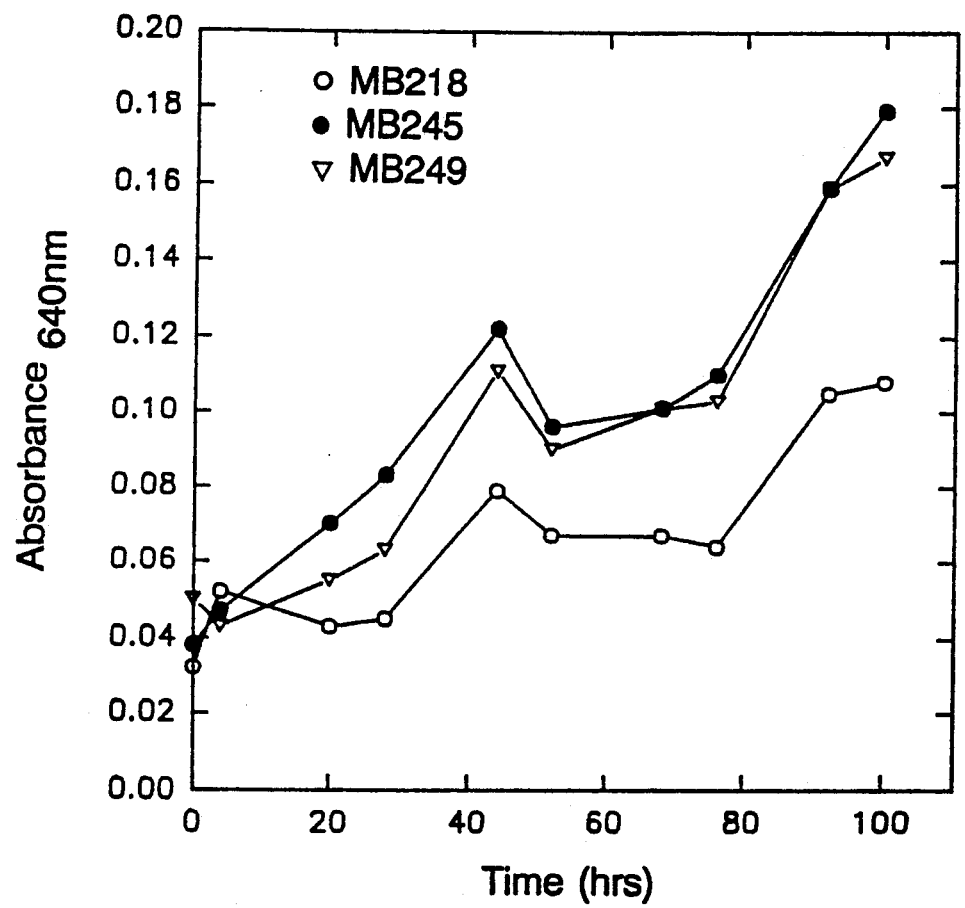
FIG. 1 compares the growth of three isolates at 6° C.

The subject invention provides a novel method for isolating useful microbes. The microbes identified by the procedures described herein can be used to control weed grasses or other unwanted vegetation. In distinct contrast to methods previously used in this area of research, the plant pathogens identified according to the subject invention are isolated from asymptomatic plants. Thus, it is possible to take microbes which naturally co-exist with plants and use these microorganisms, in appropriate concentrations and under appropriate conditions, to control certain target weeds. The target weeds controlled by the plant pathogens may be the same plant the pathogen was isolated from or the plant may be different.

For purposes of this application, a "weed" is any plant that is objectionable or interferes with the activities or welfare of man. A "herbicide" (or chemical herbicide) is a chemical used to control, suppress, or kill plants, or to severely interrupt their normal growth processes. *Herbicide Handbook of the Weed Society of America, Fifth Edition* (1983), xxi–xxiv. As used herein, the terms "bioherbicide" and "microbial herbicide" mean a biological organism used to control, suppress, or kill plants, or to severely interrupt their normal growth processes.

The present invention further relates to a method for controlling a growing weed grass which comprises applying an infective amount of a *Xanthomonas campestris* pathovar to the weed grass whereby the weed grass is selectively suppressed or killed without suppressing or killing the non-weed grasses. A "weed grass" is a grass which is undesirable or interferes with the activities or welfare of man.

the cultures of the subject invention were deposited in the Agricultural Research Service Patent Culture Collection (NRRL), Northern Regional Research Center, 1815 North University St., Peoria, Ill. 61604 USA.

| Culture | Accession No. | Deposit date |
|---|---|---|
| *Xanthomonas campestris* (MB245) | NRRL B-18855 | August 14, 1991 |
| *Xanthomonas campestris* (MA246) | NRRL B-18856 | August 14, 1991 |
| *Xanthomonas campestris* (MA249) | NRRL B-18857 | August 14, 1991 |
| *Xanthomonas campestris* (MB250) | NRRL B-18858 | August 14, 1991 |
| *Xanthomonas campestris* (MB253) | NRRL B-18859 | August 14, 1991 |
| *Xanthomonas campestris* (MB260) | NRRL B-18860 | August 14, 1991 |
| *Xanthomonas campestris* (MB276) | NRRL B-18861 | August 14, 1991 |
| *Xanthomonas campestris* (MB281) | NRRL B-18862 | August 14, 1991 |
| *Xanthomonas campestris* (MB282) | NRRL B-18863 | August 14, 1991 |
| *Xanthomonas campestris* (MB289) | NRRL B-18864 | August 14, 1991 |
| *Xanthomonas campestris* (MB290) | NRRL B-18865 | August 14, 1991 |
| *Xanthomonas campestris* (MB293) | NRRL B-18866 | August 14, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

The invention can be used to control weeds in an agricultural setting and can also be used for nonagricultural applications. For example, the invention can be used for the control of weeds in turf and as a herbicide for the management of roadside vegetation.

An important aspect of the subject invention pertains to the use of wounds on the target weed which greatly enhance the activity of the bioherbicide. The use of wounds which, in and of themselves would not control the weed, is apparently very important for the proper establishment of the bacterial infection and for appropriate access of the active ingredients to the xylem of the plant. Thus, in a preferred embodiment of the subject invention, the microbial herbicide acts directly upon the xylem of the target weed. This direct access to the xylem is facilitated by, for example, a wound or other mechanical disruption of the weed's outer layers. This access to the xylem may also be achieved through the use of chemical means for compromising the integrity of the outer layers of the plant surfaces. For example, various enzymes can be used to enhance access to the xylem. In creating a mechanical wound, the target plant can be cut, nicked, sand blasted, mowed, etc. The microbial herbicide may be applied either before or after infliction of the wound. For example, the microbial herbicide may be sprayed ahead of a mower or behind a mower. Mowing after application of the microbial herbicide enhances the establishment of the microbial herbicide in the plant's vascular system. The effectiveness of this embodiment can be enhanced by surfactants (such as silicon surfactant) which facilitate movement of the bacteria into wounds or natural openings.

One of the most surprising aspects of the novel procedures used to isolate the plant pathogens of the subject invention is the discovery that pathogens of one grass species can be isolated from asymptomatic plants of an unrelated grass. This can be seen in the case of isolate MB260 which kills annual bluegrass but does not effect goosegrass, the plant from which it was isolated. Although the isolates discovered or studied here have been manipulated in order to have them function as "plant pathogens", their more normal ecological niche (and the setting in which they are found according to the subject invention) entails cryptic survival in plants. The discovery of these advantageous phytotoxic properties through the novel method of the subject invention is highly unexpected.

We have learned that the effective host range of a new bacterial isolate is not easily predicted based on the host of origin.

Compared to the p.v. *poae* (ATCC 33804, MB238) described by Egli and Schmidt (1982), the isolates described here are much less pathogenic to rough bluegrass and much more pathogenic to annual bluegrass.

Our new isolates and pathovars, such as *poae*, do not have broad host ranges, but, they do cause a systemic wilt of certain unexpected species and some of these species are important, introduced, noxious weeds in the United States. Pathovar *poae* and many of the annual bluegrass pathogens can provide significant control of weedy species of the genus Bromus such as downy brome (*Bromus tectorum*). Pathogenicity of pathovar *poae* to Bromus has not previously been reported.

Crabgrasses (Digitaria sp.) are noxious, introduced weeds of importance in turf, but the literature does not describe any bacterial wilt disease of this host. Thus it was surprising to find that some of our annual bluegrass pathogens (MB276, MB266, MB269, for example) or other isolates have activity against that weed in wound-inoculation studies. This is another example of the benefits of our novel method of locating isolates since the best crabgrass pathogens in our collection came originally from healthy annual bluegrass samples.

Based on our observations described herein, we have discovered that there are many different organisms which are actually abundant and widespread, but whose normal ecological niche is not that of a pathogen, but more of a sub-lethal colonizer of plant xylem. These bacteria do not produce obvious "disease" in the field. The use of these organisms as biocontrol agents relies on an artificial unbalancing of this symbiosis with the host plant. When the bacterium is grown to very high population levels in pure culture and inoculated into fresh wounds—disease results. The fact that the organism does not show a proclivity towards autonomous epidemics is actually an advantage in that the artificial use as a biocontrol agent is very unlikely to result in the initiation of disease except where applied intentionally. Considering the infrequency of "disease" associated with the natural persistence of these bacteria, it is more appropriate to describe them as "xylem endophytes" rather than as "plant pathogens". What is most important is that such organisms, whatever their ecological role, have the utility of being manipulable for the purpose of weed control.

In the case of organisms which are isolated from apparently healthy tissue, there is no basis for knowing the host range a priori. Some organisms which are pathogens in certain settings can quite effectively colonize plants without causing "disease;" therefore, if they are isolated from one host, it is impossible to predict which hosts, if any, they might be able to control by way of artificial inoculation. For instance, if *Poa pratensis* (Kentucky bluegrass) is inoculated with strains such as MB218, extremely high levels ($>10^8$ cfu/cm leaf tissue) of xylem colonization occur throughout the plant; however, the plant does not exhibit disease symptoms.

This phenomenon might be referred to as "non-host" colonization, but that designation simply reflects a classification system based on disease spectrum, not a realistic ecological understanding of the organism.

The novel organisms of the subject invention are useful for the control of undesired grasses in that when the target grasses are inoculated, the bacteria systemically colonize that plant and eventually lead to wilting and death. These bacteria are safe to use on most desired grasses either because the bacterium fails to colonize systemically or because colonization does not lead to wilting and death in those cases.

The bacteria of the subject invention can be fermented using a wide range of suitable bacterial media, can be dry stabilized or stored under refrigeration, and can be applied to the target grass using a wide range of spray equipment with the exception of $CO_2$ propellants. The formulation of the bacteria can include many carriers, and inert substances such as clays, microcrystalline cellulose and celite. The formulation may also comprise protectant compounds such as sugars, proteins and complex carbohydrates which are well known in the art. As described above, the application of the bacteria can be made with an accompanying injury to the target plants (mechanical or chemical) which will facilitate the colonization of the host by the bacteria.

The *Xanthomonas campestris* which is specifically exemplified herein can be applied as an aqueous solution or on an inert carrier. The solution or carrier preferably contains between about $10^6$ to $10^{13}$ cells per gram (or ml for a solution. It will be appreciated that larger of smaller numbers of the cells per gram or ml can be used so long as infection and suppression of the weed grass is achieved.

Preferably the *Xanthomonas campestris* are provided for shipment to users in the form of a concentrate containing at least about $10^6$ cells per gram or ml, and usually about $10^{13}$ per ml, which can be lyophilized to a greater concentration and mixed with a preservative agent, the exact composition of which depends upon the method of the preservation. The cells can be frozen or lyophilized. Where the cells are frozen, glycerol or various sugars and fresh growth media can be used as preservation agents. Amounts usually between 5 and 50% by volume of the glycerol or sugars can be used. Where the cells are lyophilized, nutrient media or various sugars can be used for preservation. Generally the *Xanthomonas campestris* cells are grown to about $10^9$ to $10^{11}$ cells per ml and may then be centrifuged or otherwise concentrated by removal of growth media. They can then be frozen or lyophilized or otherwise dried. As described above, the dried bacteria can be mixed with an inorganic solid carrier such as clays, talc, inert organic material or the like which may be dusted on the grasses or mixed with water and sprayed on the grasses.

All of these variations for storing, growing and applying the *Xanthomonas campestris* cultures are well known to those skilled in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Isolation of Novel Microbes

Asymptomatic plants (plants which appeared to be completely healthy) including annual bluegrass, crabgrass, goosegrass and other species were collected from field, turf locations around the United States. Portions of these plants (leaves, stems, roots) were surface sterilized with either 10% bleach or 70% ethanol and chopped into small (1-2 mm) pieces in water, saline, or phosphate buffer and incubated with gentle mixing for 30 minutes. The buffer or water was then plated onto suitable, bacteriological media which were either basically non-selective or broadly selective (Nutrient Agar, Modified Wilbrink's Agar (MWB) or MWB with cycloheximide, 5-fluorouracil, tobramycin and methyl green—the latter medium designed to reduce the numbers of other bacteria and fungi recovered on the plates). By definition, it is not possible to use a highly selective medium because the antibiotic tolerance of an undiscovered organism cannot be known. After 2 to 10 days of growth at 22°–38° C., individual colonies were chosen from these plates and either directly inoculated to plants with needles or grown on solid or liquid media for subsequent inoculation using scissors or clippers.

Once these isolates had been successfully grown in some form of pure culture, they were inoculated to plants including the species from which they were derived and other species of interest. In the cases where desirable activity was seen, the responsible organism was either recovered from the inoculated plant or from a stock culture.

In summary, this method entails the essentially random wound inoculation screening of the internal microflora of healthy grasses with the screen being performed on the source species as well as on other species.

A list of organisms which were discovered using the method described above is presented in Table 1.

TABLE 1

| Isolate code | Origin | Isolated from | Description: target and activity |
|---|---|---|---|
| MB250 | New York | Asymptomatic Annual Bluegrass | ABG: virulent |
| MB246 | Tennesse | Asymptomatic Annual Bluegrass | ABG: virulent |
| MB245 | California, La Jolla | Asymptomatic Annual Bluegrass | ABG: virulent, more active at lower temperatures |
| MB249 | Texas, Dallas | Asymptomatic Annual Bluegrass | ABG: virulent, more active at lower temperatures |
| MB253 | Texas Tyler | Asymptomatic Annual Bluegrass | ABG: virulent |
| MB260 | Missouri | Asymptomatic Goose Grass | ABG: virulent |
| MB251 | Alabama | Asymptomatic Crabgrass | Crabgrass: leaf injury but not wilting |
| MB263 | Alabama | Asymptomatic Annual Bluegrass | ABG: low virulence |
| MB264 | Kentucky | Asymptomatic Annual Bluegrass | ABG: low virulence |
| MB281 | Louisiana | Asymptomatic Annual Bluegrass | ABG: virulent |
| MB282 | Florida | Annual Bluegrass | ABG: virulent |
| MB266 | Louisiana | Asymptomatic Annual Bluegrass | Crabgrass: low virulence |
| MB293 | Colorado | Asymptomatic Annual Bluegrass | ABG: virulent |
| MB289 | South Dakota | Asymptomatic Annual Bluegrass | ABG: virulent |
| MB290 | Washington | Asymptomatic Annual Bluegrass | ABG: virulent |
| MB276 | California, Rancho Sante Fe | Asymptomatic Annual Bluegrass | ABG: virulent, superior activity against perennial biotype. Crabgrass: |

TABLE 1-continued

| Isolate code | Origin | Isolated from | Description: target and activity |
|---|---|---|---|
| | | | moderate virulence |

Additional studies were conducted with these new isolates with the hope of finding useful variability within the now expanded collection. These experiments included temperature tolerance and host-range comparisons.

EXAMPLE 2

A Comparison of the Virulence of Isolates Under Cool Conditions

Three isolates of Xanthomonas (MB249, MB245 and MB218) were used to inoculate shake flask cultures (three separate flasks per isolate). These were grown at 22° C. for 72 hours and then used for inoculation of annual bluegrass seedlings. The separate flasks were also enumerated by dilution plate counting on Nutrient Agar. See Table 2. The inoculated plants were incubated in growth chambers with either 12 hour days at 85° F., 65° F. or 55° F. and 12 hour, nights at either 65° F., 45° F. or 35° F. respectively. Ratings of weed control were made over time. The results of these experiments are shown in Table 3.

The bacterial populations used for inoculation were very similar:

TABLE 2

| Isolate | Flask Number | Population (cfu/ml) |
|---|---|---|
| MB218 Michigan | 1 | $4 \times 10^9$ |
| | 2 | $1 \times 10^9$ |
| | 3 | $2 \times 10^9$ |
| MB245 California | 1 | $3 \times 10^9$ |
| | 2 | $3 \times 10^9$ |
| | 3 | $3 \times 10^9$ |
| MB249 Texas | 1 | $2 \times 10^9$ |
| | 2 | $3 \times 10^9$ |
| | 3 | $2 \times 10^9$ |

The California and Texas isolates caused a more rapid decline of annual bluegrass at cool temperatures although they initiated a similar level of disease at warmer temperatures:

TABLE 3

| Temp. | Isolate | Percent control of Annual Bluegrass | | | | | | | | |
|---|---|---|---|---|---|---|---|---|---|---|
| | | Day 9 | Day 13 | Day 15 | Day 20 | Day 26 | Day 36 | Day 41 | Day 53 | Day 62 |
| 85° F./65° F. (warm) | MB218 | 70 | 80 | 99 | 100 | 100 | 100 | 100 | 100 | 100 |
| | MB245 | 70 | 90 | 99 | 100 | 100 | 100 | 100 | 100 | 100 |
| | MB249 | 75 | 95 | 99 | 100 | 100 | 100 | 100 | 100 | 100 |
| 65° F./45° F. (cool) | MB218 | 0 | 0 | 30 | 65 | 75 | 95 | 100 | 100 | 100 |
| | MB245 | 0 | 60 | 75 | 85 | 90 | 99 | 100 | 100 | 100 |
| | MB249 | 0 | 40 | 70 | 85 | 90 | 99 | 100 | 100 | 100 |
| 55° F./35° F. (cold) | MB218 | 0 | 0 | 0 | 0 | 0 | 0 | < | 37 | 48 |
| | MB245 | 0 | 0 | 0 | 0 | 0 | 25 | 45 | 80 | 85 |
| | MB249 | 0 | 0 | 0 | 0 | 0 | 15 | 25 | 83 | 85 |

Although the annual bluegrass isolates in Table 1 have proven to be very similar in extensive host range studies and in biochemical characterizations, some virulence differences have been observed as noted in Tables 1 and 3. Two isolates were able to provide control of annual bluegrass at low temperatures. The ability to control weed grasses at low temperatures is a critical attribute because it is very desirable to control annual bluegrass, a winter annual, early in the season before it produces seedheads and before it can become established as large spots in the turf.

The temperature response differences which have been detected between isolates are large enough to establish that these are separate strains. The most virulent strains under cool conditions are MB249 and MB245. We have studied the plasmid profiles of these strains and using that method, it is possible to distinguish them from any previously reported strains. Strain MB218 contains a single plasmid (approximately 35 Kb) with 3 bands after digestion with EcoRI. Strain MB249 contains three similar bands and two new bands after EcoRI digestion. Strain MB245 contains no plasmid. This difference is useful for showing that these are distinct isolates.

Only by conducting the asymptomatic plant discovery program, described and claimed here, was it possible to sufficiently expand the base of isolates in order to demonstrate an underlying variability among isolates relative to cool temperature virulence.

EXAMPLE 3

Host Range of Xanthomonas Isolates

Broth cultures of various Xanthomonas isolates were grown in either nutrient broth or Modified Wilbrink's medium for 72 hours at room temperature. These were diluted, if necessary, to achieve an approximate cell concentration of $10^9$ cfu/ml. Scissors, alcohol sterilized and flamed between isolates, were dipped into the cell suspensions and used to cut seedling plants of various species. The plants were incubated in the greenhouse and observed for symptoms. The results are presented in Tables 4 and 5.

TABLE 4

Susceptibility among Bromus species (Ratings: + + > 70% control; + 30-70% control; - no control observed in this test)

| Target species | MB218 | MB249 | pathovar graminis | pathovar poae |
|---|---|---|---|---|
| fasiciculatus | + + | + + | − | + + |
| sericeus | + + | + + | − | + + |
| hordeaceus | + + | + + | − | + + |
| madritensis | + + | + + | − | + + |
| scoparius | + + | + + | + + | + + |
| tectorum | + + | + + | + + | + + |
| antolicus | + + | + + | + | + + |
| danthoniae | + + | + + | + | + + |
| oxtodon | + + | + + | + | + + |
| erectus | − | + | − | + + |
| alopecurus | − | + | − | + + |
| secalinus | − | − | + + | − |
| rubens | − | − | − | + |
| anomalus | − | + | − | − |
| pseudodanthoniae | + + | + + | − | + + |
| sewerzovii | − | − | + + | − |
| mollis | + | + | − | + |
| squarrosus | − | + | + | − |
| rigidus | + | + + | − | + |
| macranthos | − | + | − | − |
| arduennsnis | − | + | − | − |

TABLE 5

Susceptibility of crabgrass to Xanthomonas isolates

| Isolate | Percent Kill of Crabgrass | Percent kill of annual bluegrass |
|---|---|---|
| MB276 | 44 | 100 |
| MB218 | 20 | 100 |
| MB249 | 0 | 100 |
| MB282 | 3 | 100 |

EXAMPLE 4

Low Temperature Fermentation Comparison

Three isolates of *Xanthomonas campestris* were aseptically inoculated to Nutrient broth and grown in shake-flasks in a temperature controlled shaking incubator at a constant 6° C. At intervals after inoculation, the growth of the cells was monitored based on light scattering by measuring the absorbance at 640 nm using a Specronic-20 spectrophotometer. Under these conditions the strains MB245 and MB249 achieved higher cell densities more rapidly than did strain MB218 (FIG. 1). More rapid achievement of high cell densities has also been noted at warmer temperatures in shake flasks and in fermenter. Thus, these strains show superior characteristics for growth in liquid culture at less than or equal to room temperature.

EXAMPLE 5

Increased Turfgrass Safety

Isolates of *Xanthomonas campestris* were grown for 72 hours at room temperature in modified Wilbrink's broth and used for inoculation of a wide range of seedling plantings of turfgrass cultivars. The cell density of the broths was monitored by standard, dilution plating methods to insure saturation inoculum levels for a host range test. Plants were then incubated in the greenhouse and monitored for systemic wilt symptoms characteristic of infection by these pathogens. Positive controls of susceptible species (annual bluegrass) were included with each test as were comparison inoculations with known pathovars of any grass species being tested. The vast majority of desirable turfgrasses were not at all susceptible to any of the Xanthomonas isolates, but in some cases specific cultivars showed differential susceptibility to the different isolates. A summary of these observations are listed in Table 6 below. The susceptibility of a cultivar is rated as "slight" if occasional seedlings demonstrate wilt symptoms. The susceptibility is listed as "moderate" if between 20 and 50 percent of the seedlings wilt. The susceptibility is listed as "high" if most of the seedlings wilt.

TABLE 6

| Turfgrass Species | Cultivar | Level of Susceptibility to: MB218 | MB245 |
|---|---|---|---|
| Creeping red fescue | 'Dawson' | slight | none |
| Perennial rygrass | 'Derby' | slight | none |
| Kentucky bluegrass | 'Midnight' | moderate | slight |
|  | 'Ram I' | high | slight to moderate |
|  | 'Tendos' | high | slight |

The low rates of injury to desired turfgrasses caused by the Xanthomonas isolates makes it possible to control weed grasses which are mixed in with turfgrasses without harming the desired turfgrasses. Thus, the isolates of the subject invention may be safely applied to turfgrasses for the control of, for example, annual bluegrass, Bromus species, Digitaria species, and *Poa annua* var. *reptans*.

EXAMPLE 6

Accelerated Control of Annual Bluegrass Using a Combination of *Xanthomonas campetris* Isolates and a Plant Growth Regulator, Mefluidide Small pots of greenhouse grown, seedling annual bluegrass were sprayed with Xanthomonas cell suspensions of two different strains: MB245 ($4 \times 10^9$ cfu/ml) and MB218 ($3 \times 10^9$ cfu/ml) alone or in combination with mefluidide (Embark TM) at rates of 0.03 or 0.15%. Control plants were sprayed with water or the same rates of mefluidide used in the combinations. Plants were approximately 6 cm tall when sprayed with the suspensions/solutions at the rate of 100 gallons per acre. While still wet with the spray material, they were cut to a height of 5 cm. The plants were then placed in a growth chamber with 12 hour, 45° F. nights and 12 hour 65° F. days. The effect of the treatments were quantified 10 and 14 days later by measuring the fresh weight of all grass above the soil line (Table 7). Reduced weight is attributable to the effects of the growth regulator or to the wilting effect of the bacterium, depending on the treatment.

TABLE 7

Accelerated control using Xanthomonas in combination with the plant growth regulator, mefluidide

| Bacterium | Mefluidide concentration | Fresh weight 10 DAT (grams) | Fresh weight 14 DAT (grams) |
|---|---|---|---|
| — | — | 1.01 | 8.04 |
| MB245 | — | 0.64 | 0.58 |
| MB218 | — | 1.22 | 2.02 |
| — | 0.03% | 0.65 | 6.26 |
| — | 0.15% | 0.46 | 1.42 |
| MB245 | 0.03% | 0.28 | 0.38 |
| MB245 | 0.15% | 0.25 | 0.11 |
| MB218 | 0.03% | 0.42 | 0.98 |
| MB218 | 0.15% | 0.24 | 0.12 |

These data demonstrate that the advantageous herbicidal effect of the bacteria can be enhanced and/or accelerated by the use of plant growth regulator. A variety of growth regulators are known to those skilled in this art and could be used according to the teachings provided herein.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for control of annual bluegrass comprising applying to said annual bluegrass of a herbicidally effective amount of a microorganism selected from the group consisting of: MB245 (NRRL B-18855), MB249 (NRRL B-18857), and MB276 (NRRL B-18861).

2. A method for the control of Digitaria species (crabgrass) comprising applying to said crabgrass of a herbicidally effective amount of a microorganism selected from the group consisting of microorganisms having all the identifying characteristics of the following isolates: MB245 (NRRL B-18855), MB249 (NRRL B-18857), and MB276 (NRRL B-18861).

3. The method, according to claim 2, wherein said microorganism has the identifying characteristics of MB276.

4. A method for control of Bromus species comprising applying to said Bromus species of a herbicidally effective amount of a microorganism selected from the group consisting of microorganisms having all the identifying characteristics of the following isolates: MB245 (NRRL B-18855), MB249 (NRRL B-18857), and MB276 (NRRL B-18861).

5. A method for control of *Poa annua* var. *reptans* (perennial form of *Poa annua*) comprising applying to said *Poa annua* var. *reptans* of a herbicidally effective amount of a microorganism selected from the group consisting of microorganisms having all the identifying characteristics of the following isolates: MB245 (NRRL B-18855), MB249 (NRRL B-18857), and MB276 (NRRL B-18861).

6. The method, according to claim 5, wherein said microorganism has all the identifying characteristics of MB276 (NRRL B-18861).

* * * * *

UNITED STATES PATENT AND TRADEMARK OFFICE
CERTIFICATE OF CORRECTION

PATENT NO. : 5,271,932
DATED      : Dec. 21, 1993
INVENTOR(S) : Steven D. Savage, et al It is certified that error appears in the above-indentified patent and that said Letters Patent is hereby corrected as shown below:

Column 2   line 10: Delete "Electronic" and insert --Electron--.

Column 3   line 28: Delete "the" and insert --The--.

Column 7   line 30 (Table 1): Delete "Tennesse" and insert --Tennessee--.

Signed and Sealed this

Fifth Day of July, 1994

Attest:

BRUCE LEHMAN

Attesting Officer        Commissioner of Patents and Trademarks